United States Patent
Pechstein et al.

(10) Patent No.: US 6,705,898 B2
(45) Date of Patent: Mar. 16, 2004

(54) CONNECTOR FOR CONNECTING A TRANSMISSION LINE TO AT LEAST ONE SENSOR

(75) Inventors: Torsten Pechstein, Radebeul (DE); Reiner Franzheld, Waldheim (DE); Katrin Scholz, Bobritzsch (DE)

(73) Assignee: Endress + Hauser Conducta Gesellschaft fur Mess-und Regeltechnik mbH +Co., Gerlingen (DE)

( * ) Notice: Subject to any disclaimer, the term of this patent is extended or adjusted under 35 U.S.C. 154(b) by 0 days.

(21) Appl. No.: 09/985,748

(22) Filed: Nov. 6, 2001

(65) Prior Publication Data

US 2002/0102884 A1 Aug. 1, 2002

(30) Foreign Application Priority Data

Nov. 7, 2000 (DE) .......................... 100 55 090

(51) Int. Cl.⁷ .......................... H01R 24/00; H01R 33/00
(52) U.S. Cl. .......................... 439/660; 439/950
(58) Field of Search .................. 439/660, 557, 439/577, 950; 336/90; 333/242; 235/451

(56) References Cited

U.S. PATENT DOCUMENTS

| | | | | | |
|---|---|---|---|---|---|
| 3,387,606 | A | * | 6/1968 | Crafts et al. | 336/90 |
| 4,225,748 | A | * | 9/1980 | Buck et al. | 174/52.1 |
| 5,341,083 | A | * | 8/1994 | Klontz et al. | 320/109 |
| 5,386,196 | A | * | 1/1995 | Jones et al. | 324/667 |
| 6,236,119 | B1 | * | 5/2001 | Bonn et al. | 307/10.1 |
| 6,476,520 | B1 | * | 11/2002 | Bohm et al. | 307/104 |
| 6,533,283 | B1 | * | 3/2003 | Gottel | 277/317 |
| 2002/0018513 | A1 | * | 2/2002 | Curry et al. | 374/178 |

FOREIGN PATENT DOCUMENTS

| | | |
|---|---|---|
| DE | 195 40 854 | 11/1995 |
| EP | 1 014 512 | 12/1999 |

* cited by examiner

*Primary Examiner*—Michael C. Zarroli
(74) *Attorney, Agent, or Firm*—Hoffman, Wasson & Gitler P.C.

(57) ABSTRACT

The invention relates to a connector comprising a plug element and a socket element which can be detachably connected to the plug element for connection of a transmission line to at least one sensor. This connection prevents moisture, dust or dirt particles and corrosive substances penetrating between the plug element and the socket element from adversely affecting the signal transmission between the plug element and the socket element. The connector utilizes an inductive, optical or capacitive contactless signal transmission between the plug element and the socket element.

26 Claims, 2 Drawing Sheets

CONNECTOR FOR CONNECTING A TRANSMISSION LINE TO AT LEAST ONE SENSOR

FIELD OF THE INVENTION

The present invention relates to a connector comprising a plug element and a socket element which can be detachably connected to the plug element, for connection of a transmission line to at least one sensor.

The invention moreover relates to a socket element of a connector which can be detachably connected to the plug element of the connector, the connector being used to connect a transmission line to at least one sensor.

Furthermore, this invention relates to the plug element of a connector which can be detachably connected to the socket element of the connector, the connector being used to connect a transmission line to at least one sensor.

Finally, this invention also relates to a process for signal transmission between the plug element of a connector and the socket element of the connector which can be detachably connected to the plug element. Additionally a transmission line can be connected to at least one sensor by means of the connector.

The plug element can be assigned to at least one sensor and the socket element to the transmission line. Alternatively at least one sensor however can also be provided with a socket element, the transmission line then being assigned to the plug element.

BACKGROUND OF THE INVENTION

A transmission line which is connected via a connector to at least one sensor is used to transmit a measurement signal from one sensor and/or for transmission of a power supply signal for the sensor. In the connectors known from the prior art, the measurement signals and/or the power supply signals are transmitted by means of an electrically conductive connection between the socket element and the plug element via the connector. To be able to establish an electrically conductive connection between the socket element and the plug element of the connector, on the socket element and on the plug element, there must be electrical contact elements of an electrically conductive material which come into contact with one another when the socket element and the plug element are connected to one another.

Especially when a connector is used in a moist or chemically corrosive environment, high demands must be imposed on the connector with respect to tightness and electrical insulation properties. The penetration of moisture, dust or dirt particles and corrosive substances for example could lead to a short circuit between the electrical contact elements of the connector or to corrosion of the contact elements. Reliable measurement by evaluation of the measurement signal and/or reliable supply of at least one sensor with electric power is thus adversely affected or even becomes impossible.

SUMMARY OF THE INVENTION

Therefore the object of this invention is to connect a transmission line by means of a connector to at least one sensor such that moisture, dust or dirt particles and corrosive substances cannot adversely affect the signal transmission properties via the connector.

To achieve this object, the invention, proceeding from the connector of the initially mentioned type, proposes that the connector has means for implementing contactless signal transmission between the plug element and the socket element.

The connector of the present invention can be used to connect a transmission line to a single sensor or to a measurement means with several sensors. Via the connector, a power supply signal can be transmitted to the sensor or to the measurement means with several sensors, as can a measurement signal from the sensor or several measurement signals from the measurement means. The connector can be used for pH, pressure, temperature, cloudiness, chloride, oxygen, conductivity and any other sensors.

Contactless signal transmission can be accomplished in different ways. Thus, for example, optical, inductive or capacitive signal transmission are conceivable. To do this, in the socket element and the plug element of the connector there must be a suitable means for implementation of the corresponding contactless signal transmission.

The plug element can be assigned to at least one sensor and the socket element to the transmission line. Alternatively, at least one sensor however can also be provided with a socket element, the transmission line then being assigned to the plug element.

To connect the transmission line to at least one sensor, the plug element is plugged into the socket element in the conventional manner. When the socket element and the plug element are plugged together there is however no electrically conductive connection between the contact elements of the socket element and the contact elements of the plug element, as in the prior art. Rather, by plugging the plug element and socket element into one another the means for accomplishing contactless signal transmission in the socket element and the plug element are moved into a defined position relative to one another so that reliable contactless signal transmission can takes place via the connector.

Since no electrical contact elements need be routed out of the socket element and the plug element, the socket element and plug element can be completely sealed to the outside. Even if the seal between the socket element and plug element cannot completely prevent the penetration of moisture, dust or dirt particles and corrosive substances, the penetrating substances cannot penetrate into the socket element itself or the plug element itself. When the socket element and plug element are plugged into one another a gap can form between the socket element and the plug element. Moisture, dust or dirt particles and corrosive substances which have penetrated into this gap have almost no effect on the signal transmission behavior between the socket element and the plug element and do not adversely affect contactless signal transmission.

With the connector of the present invention, a connection of one transmission line to at least one sensor can be accomplished, in which moisture, dust or dirt particles and corrosive substances do not adversely affect transmission behavior. The connector as claimed in the invention can furthermore prevent leakage currents between at least one sensor and a measuring transducer connected to the end of the transmission line by metallic isolation. The use of an equipotential bonding line or similar means can be abandoned. Moreover the plug element as claimed in the invention is protected especially against explosion. Another advantage of the connector as claimed in the invention is the possibility of a uniform, i.e. completely enclosed, configuration of the plug and socket housing. In this way higher mechanical strength can be achieved.

According to one advantageous development of this invention, it is proposed that the connector has means for accomplishing inductive signal transmission between the plug element and the socket element.

According to one preferred embodiment of this invention, it is proposed that the plug element has a first coil element with the first part of a ferrite core transformer and the socket element has a second coil element with the second part of the ferrite core transformer. The measurement signals or power supply signals to be transmitted via the connector are transmitted with certain frequencies. The measurement signal of a sensor can first be amplified and then converted into a frequency-analogous signal. The measurement signal is then transmitted with a certain frequency inductively to the transmission line and further to the measuring transducer. The power supply signal can likewise be transmitted with a certain frequency via the connector and can be used for power supply of the means for accomplishing inductive signal transmission and of at least one sensor. The core material and the models of the transformer influence the transmitted power of the connector. The choice of a suitable core material and a suitable model of the transformer can be sensor-specific and application-specific and it can be made with consideration of costs.

Advantageously, in the plug element and socket element there is at least one filter each for separation of the measurement signal from one sensor and of a power supply signal for the one sensor or for each sensor.

According to one alternative advantageous development of this invention, it is proposed that the connector has means for accomplishing signal transmission between the plug element and the socket element. Optical signal transmission can take place in any frequency range, with visible or invisible light.

According to one preferred embodiment of this invention, it is proposed that the plug element and the socket element have housing areas of a material which is optically transmissive at least for the frequency range which is relevant to signal transmission.

The optically transmissive areas are advantageously located facing one another when the plug element and the socket element are connected to one another. Thus the optical signals for signal transmission can be easily transmitted from the socket element to the plug element and vice versa.

The plug element preferably has one transmitting or receiving element of at least one optical coupler and the socket element has a receiving and transmitting element of at least one optical coupler, which element is assigned to the transmitting or receiving element.

According to still another advantageous development of this invention, it is proposed that the plug element has means for accomplishing capacitive signal transmission between the plug element and the socket element. Advantageously, the plug element has a first capacitive body of a capacitor and the socket element has a second capacitive body of a capacitor. In the simple case the capacitive bodies are made for example as plates of a plate capacitor, the plug element and the socket element each having one plate.

According to one preferred embodiment of this invention, it is proposed that the plug element or socket element assigned to the sensor or to each sensor has an operational amplifier. The operational amplifier amplifies the measurement signal of one sensor or each sensor before it is transmitted via the connector by contactless signal transmission.

According to another preferred embodiment of this invention, it is proposed that the plug element or socket element assigned to the sensor or each sensor has a voltage-controlled oscillator (VCO) for converting the measurement signal of the sensor into a frequency-analogous signal. The voltage-controlled oscillator converts the measurement signal of the sensor before contactless signal transmission into a frequency-analogous signal. Therefore, a voltage measurement signal is not transmitted, but a frequency-analogous signal is transmitted, which is much less susceptible to interference than the voltage measurement signal.

The object of the invention is furthermore achieved proceeding from the socket element of a connector of the initially mentioned type by the socket element having means for implementing contactless signal transmission to the plug element which interact with the corresponding means of the plug element.

According to one advantageous development of this invention, it is proposed that the socket element has means for implementing inductive signal transmission to the plug element.

According to another advantageous development of this invention it is proposed that the socket element has means for accomplishing optical signal transmission to the plug element.

According to another advantageous development of this invention, it is proposed that the socket element has means for accomplishing capacitive signal transmission to the plug element.

The object of this invention is furthermore achieved proceeding from the plug element of a connector of the initially mentioned type by the plug element having means for implementing contactless signal transmission to the socket element, which means interact with the corresponding means of the socket element.

According to one advantageous development of this invention, it is proposed that the plug element has means for implementing inductive signal transmission to the socket element.

According to another advantageous development of this invention, it is proposed that the plug element has means for accomplishing optical signal transmission to the socket element.

According to another advantageous development of this invention, it is proposed that the plug element has means for accomplishing capacitive signal transmission to the socket element.

Finally, the object of this invention is achieved proceeding from the process for signal transmission of the initially mentioned type by signal transmission between the plug element and the socket element being accomplished without contact.

According to one advantageous development of this invention, it is proposed that signal transmission between the plug element and the socket element is accomplished inductively.

According to another advantageous development of this invention, it is proposed that signal transmission between the plug element and the socket element is accomplished optically.

According to still another advantageous development of this invention, it is proposed that signal transmission between the plug element and the socket element is accomplished capacitively.

BRIEF DESCRIPTION OF THE DRAWINGS

Other features, possible applications and advantages of the invention arise from the following description of embodiments of the invention which are shown in the drawings. Here all the described features in and of themselves or in combination form the subject matter of the invention, regardless of their summary in the claims or their referencing and regardless of their formation or representation in the specification or the drawings.

DETAILED DESCRIPTION OF THE DRAWINGS

Figure 1:
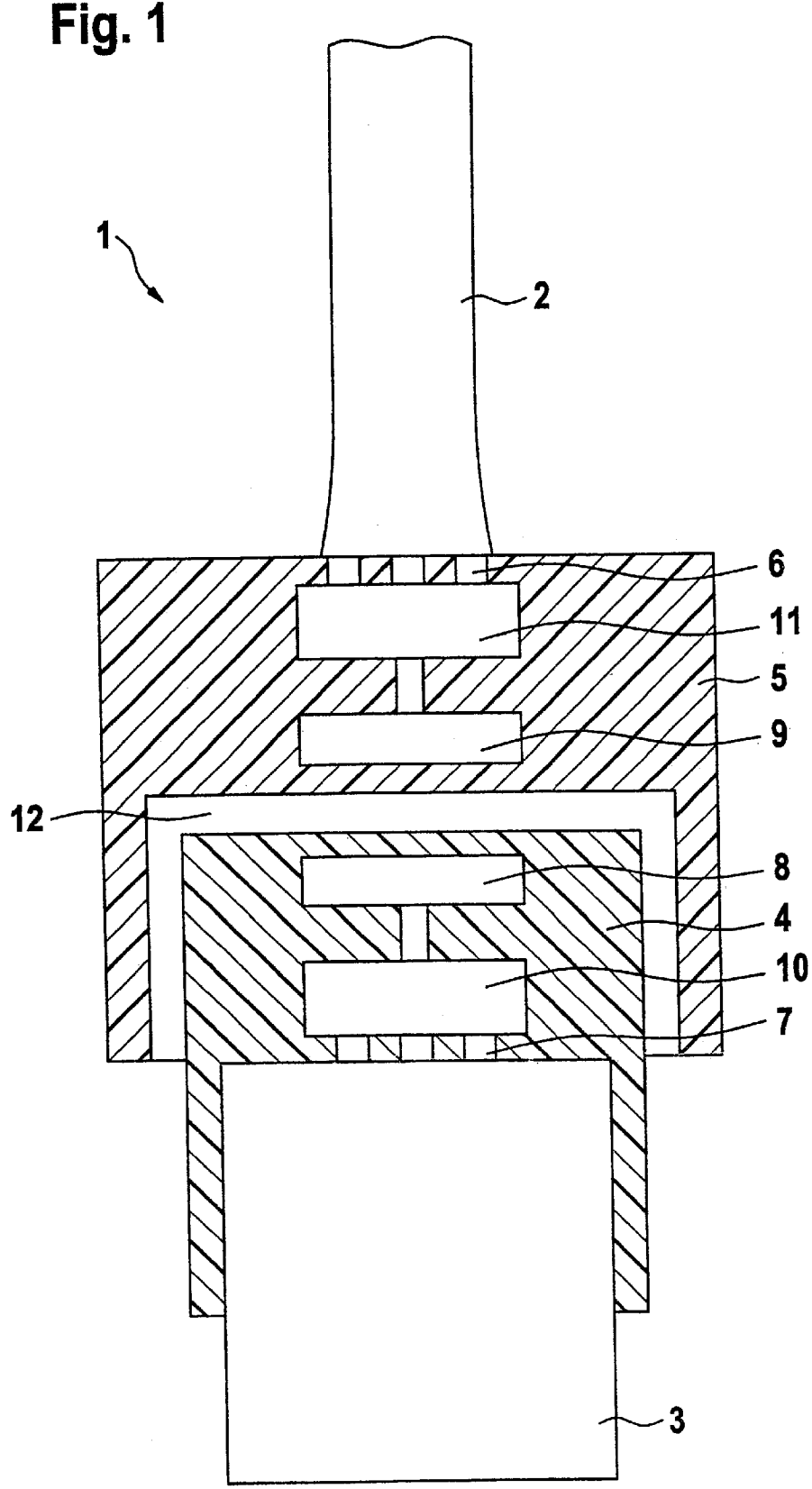
FIG. 1 shows a connector as claimed in the invention according to a first preferred embodiment in a section.

FIG. 1 shows a connector as claimed in the invention in its totality labelled with reference number 1. The connector 1 is used to connect a transmission line 2 to a sensor 3, for example a sensor for process measurement engineering, for measuring the pH, pressure, temperature, cloudiness, chloride content, oxygen content or conductivity. Instead of for connection of only one sensor 3, as shown in FIG. 1, the connector 1 can also be used to connect several sensors which can be combined into a common measurement means.

The connector 1 comprises a plug element 4 and a socket element 5 which is detachably connected to the plug element 4. The transmission line 2 is connected to the socket element 5 by means of electrical contact-making 6. The connection is sealed by suitable means to prevent penetration of moisture, dust or dirt particles and corrosive or caustic substances into the area of electrical contact-making 6. The transmission line 2 is attached for example by an injection-molding casting process to the socket element 5. The plug element 4 is connected to the sensor 3 by means of electrical contact-making 7. There is a suitable seal in the area of the terminal in order to prevent penetration of moisture, dust or dirt particles and corrosive substances into the area of electrical contact-making 7. The plug element 4 is attached to the sensor 3 for example by an injection-molding casting process.

One decisive difference between the connector 1 of the present invention and the connectors known from the prior art is the contactless signal transmission between the plug element 4 and the socket element 5. In the embodiment from FIG. 1 the signal is transmitted inductively. To do this, the plug element 4 has a first coil element 8 with the first part of a ferrite core transformer. The socket element 5 has a second coil element 9 with the second part of a ferrite core transformer. The first coil element 8 can also be regarded as the primary side of the transformer and the second coil element 9 as the secondary side of the transformer.

A power supply signal from a power source can be transmitted via the connector 1 to supply the sensor 3 with electrical power, as can measurement signals from the sensor 3 to a measuring transducer. The power source and the measuring transducer are connected to the socket element 5 by means of the transmission line 2, but this is not shown in FIG. 1. To transmit the power supply signal, the second coil element 9 is supplied with a certain frequency. The power supply signal is transmitted with this frequency to the first coil element 8 and then rectified. There are suitable electronics 10 in the plug element 4 for rectification. The rectified power supply signal is used as the power supply voltage for the electronics 10 within the plug and for the sensor 3.

The electronics 10 within the plug comprise moreover an operational amplifier (not shown) which amplifies the measurement signal of the sensor 3. The operational amplifier can be made as an impedance converter with a gain v=1. Furthermore, the electronics 10 within the plug comprise a voltage-controlled oscillator (VCO or V/F converter) which converts the voltage measurement signal into a frequency-analogous signal. The frequency of this frequency-analogous signal is dependent on the voltage value of the measurement signal. The frequency-analogous signal is transmitted via the same coil elements 8, 9 which are also used for transmission of the power supply signal. To separate the measurement signal from the power supply signal, there are primary-side and secondary-side filters (not shown) in the electronics 10 within the plug and the electronics 11 within the socket.

When the plug element 4 and the socket element 5 are connected to one another, there is a narrow gap 12 between the plug element 4 and the socket element 5. For the connector 1 of the present invention, no special precautions need be taken to seal the gap 12 and prevent the penetration of moisture, dust or dirt particles and corrosive substances. Contrary to the connectors known from the prior art, in which in the area of the gap there are electrical contact-making elements which can be short circuited or corroded by substances which have penetrated, the penetrating substances in the connector 1 of the present invention have no adverse effect on the signal transmission behavior between the plug element 4 and the socket element 5. Moreover leakage currents between the sensor 3 and the measuring transducer are prevented by metallic isolation by the connector 1 as claimed in the invention.

Figure 2:
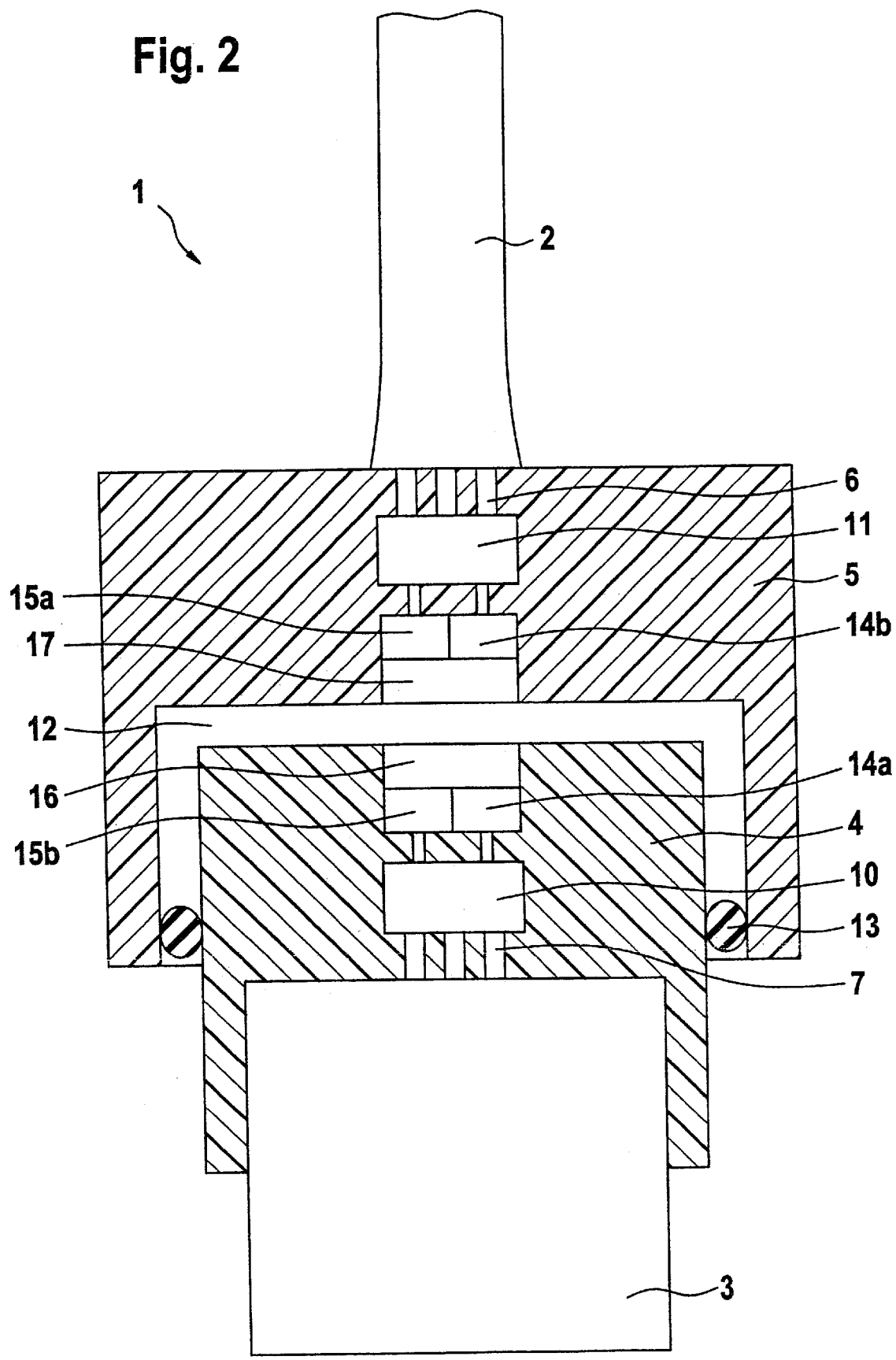
FIG. 2 shows a connector as claimed in the invention according to a second preferred embodiment in a section.

FIG. 2 shows a second preferred embodiment of the connector 1 as claimed in the invention. The connector 1 according to the second embodiment differs from the connector 1 from FIG. 1 primarily by the fact that signal transmission takes place without contact by optical means. Furthermore, the gap 12 between the plug element 4 and the socket element 5 is sealed by suitable sealing means 13, for example a rubber ring, to prevent penetration of moisture, dust or dirt particles and corrosive substances. The transmission line 2 is attached by mechanical mounting or an injection-molding casting process to the socket element 5. The plug element 4 is integrated as an integral component of the sensor 3 into its housing.

To implement optical signal transmission, an optical coupler is used. Optical signal transmission can take place at any frequencies (for example with UV, IR or visible light). To be able to accomplish bidirectional signal transmission, the plug element 4 has a transmitting element 14a of a first optical coupler and a receiving element 15b of a second optical coupler. The socket element 5 comprises a corresponding receiving element 14b of the first optical coupler and the transmitting element 15a of the second optical coupler. The plug element 4 and the socket element 5 have housing areas 16, 17 which consist of a material which is optically transmissive at least for the frequency range which is relevant for signal transmission. The optically transmissive housing areas 16, 17 consist for example of a transparent plastic, plexiglass or glass. FIG. 2 clearly shows that the optically transmissive areas 16, 17 are arranged facing one another when the plug element 4 and the socket element 5 are connected to one another.

In optical signal transmission, power supply of the sensor 3 take place as before inductively or capacitively. But if it should be possible to integrate means for accomplishing optical signal transmission in the small space of a plug element 4 or socket element 5, which means can transmit signals with a relatively high power, there is nothing to prevent transmission of the power supply signal optically. Via the bidirectional optical connection, for example, in one direction, trigger signals for control of certain sensor functions can be transmitted to the sensor 3 and in the other direction measurement signals from the sensor 3.

What is claimed is:

1. A connector for connecting a transmission line to at least one sensor, comprising:
    a plug element connected to the at least one sensor;
    a socket element connected to the transmission line;
    a contactless connection device between said plug element and said socket element; and
    wherein a power signal is supplied to the at least one sensor and a measurement signal is produced by the at least one sensor, further wherein a first filter element is provided within said plug element and a second filter element is provided within said socket element for separating the measurement signal from the power signal.

2. The connector in accordance with claim 1, wherein said contactless connection device provides an inductive signal transmission between said plug element and said socket element.

3. The connector in accordance with claim 1, wherein said contactless connection device provides an optical signal transmission between said plug element and said socket element.

4. The connector in accordance with claim 1, wherein said contactless connection device provides a capacitive signal transmission between said plug element and said socket element.

5. The connector in accordance with claim 2, wherein said plug element further includes a first coil element having a first part of a ferrite core transformer and said socket element further includes a second coil element and a second part of a ferrite core transformer.

6. The connector in accordance with claim 3, wherein said plug element and said socket element are provided with optically transmissive material, at least for a frequency range relevant to said optical signal transmission.

7. The connector in accordance with claim 6, wherein said optically transmissive material in said plug element and said socket element face one another when said plug element and said socket element are connected to one another.

8. The connector in accordance with claim 6, wherein said plug element includes a transmitting or receiving element and said socket element is provided with a transmitting or receiving element forming an optical coupler between said plug element and said socket element.

9. The connector in accordance with claim 7, wherein said plug element includes a transmitting or receiving element and said socket element is provided with a transmitting or receiving element forming an optical coupler between said plug element and said socket element.

10. The connector in accordance with claim 4, wherein said plug element includes a first capacitive body of a capacitor and said socket element includes a second capacitive body of a capacitor.

11. The connector in accordance with claim 1, wherein said plug element or said socket element is provided with an operational amplifier.

12. The connector in accordance with claim 1, wherein said plug element or said socket element is provided with a voltage controlled oscillator.

13. The connector in accordance with claim 1, wherein said plug element or said socket element is provided with a voltage controlled oscillator for converting the measurement signal into a frequency-analogous signal.

14. The connector in accordance with claim 1, further including a means provided in said plug element and said socket element for accomplishing digital signal transmission between said plug element and said socket element.

15. A socket element of a connector detachably connected to a plug element for connecting a transmission line to at least one sensor, said socket element comprising:

a contactless connection device provided within the socket element for transmitting a signal to the plug element; and wherein a power signal is supplied to the at least one sensor and a measurement signal is produced by the at least one sensor, and further wherein a first filter element is provided within said plug element and a second filter element is provided within said socket element for separating the measurement signal from the power signal.

16. The socket element in accordance with claim 15, wherein said contactless connection devices provides an inductive signal transmission between the socket element and the plug element.

17. The socket element in accordance with claim 15, wherein said contactless connection devices provides an optical signal transmission between the socket element and the plug element.

18. The socket element in accordance with claim 15, wherein said contactless connection devices provides a capacitive signal transmission between the socket element and the plug element.

19. A plug element of a connector detachably connected to a socket element for connecting a transmission line to at least one sensor, said plug element comprising:

a contactless connection device provided within the plug element for transmitting a signal to the socket element; and wherein a power signal supplied to the at least one sensor and a measurement signal is produced by the at least one sensor, and further wherein a first filter element is provided within said plug element and a second filter element is provided within said socket element for separating the measurement signal from the power signal.

20. The plug element in accordance with claim 19, wherein said contactless connection device provides an inductive signal transmission between the plug element and the socket element.

21. The plug element in accordance with claim 19, wherein said contactless connection device provides an optical signal transmission between the plug element and the socket element.

22. The plug element in accordance with claim 19, wherein said contactless connection device provides a capacitive signal transmission between the plug element and the socket element.

23. A process for transmitting a signal between a transmission line and at least one sensor through a connector comprising a plug element and a socket element, comprising the steps of:

detachably connecting the plug element to the socket element;

providing a contactless connector between the plug element and the socket element;

supplying a power signal to the at least one sensor; and filtering the transmitted signal in the plug element or the socket element for separating the measurement signal from the power signal.

24. The process in accordance with claim 23, wherein said contactless connection is accomplished inductively.

25. The process in accordance with claim 23, wherein said contactless connection is accomplished optically.

26. The process in accordance with claim 23, wherein said contactless connection is accomplished capacitively.

* * * * *